US012767683B2

(12) United States Patent
Zhang et al.

(10) Patent No.: US 12,767,683 B2
(45) Date of Patent: Oct. 20, 2026

(54) METHOD FOR PURIFYING SUCRALOSE

(71) Applicant: ANHUI JINHE INDUSTRIAL CO., LTD., Chuzhou (CN)

(72) Inventors: Zhengsong Zhang, Chuzhou (CN); Rui Zhou, Chuzhou (CN); Jingang Zhao, Chuzhou (CN); Xuelian Zheng, Chuzhou (CN); Yongfeng Bu, Chuzhou (CN); Yongle Chen, Chuzhou (CN)

(73) Assignee: ANHUI JINHE INDUSTRIAL CO., LTD., Chuzhou (CN)

( * ) Notice: Subject to any disclaimer, the term of this patent is extended or adjusted under 35 U.S.C. 154(b) by 672 days.

(21) Appl. No.: 18/247,066

(22) PCT Filed: Sep. 30, 2020

(86) PCT No.: PCT/CN2020/119233
§ 371 (c)(1),
(2) Date: Mar. 28, 2023

(87) PCT Pub. No.: WO2022/067621
PCT Pub. Date: Apr. 7, 2022

(65) Prior Publication Data

US 2023/0374054 A1 Nov. 23, 2023

(51) Int. Cl.
*C07H 5/02* (2006.01)
*C07H 1/06* (2006.01)

(52) U.S. Cl.
CPC ................. *C07H 5/02* (2013.01); *C07H 1/06* (2013.01)

(58) Field of Classification Search
CPC .................................... C07H 5/02; C07H 1/06
See application file for complete search history.

(56) References Cited

U.S. PATENT DOCUMENTS

| | | | |
|---|---|---|---|
| 4,980,463 | A | 12/1990 | Walkup et al. |
| 5,498,709 | A | 3/1996 | Navia et al. |
| 7,049,435 | B2 | 5/2006 | Catani et al. |
| 2006/0188629 | A1 | 8/2006 | Liesen et al. |
| 2009/0312538 | A1 | 12/2009 | Deshpande et al. |

FOREIGN PATENT DOCUMENTS

| | | | | | |
|---|---|---|---|---|---|
| CN | 1639179 | A | | 7/2005 | |
| CN | 101177437 | A | * | 5/2008 | ............... C07H 5/02 |
| CN | 101210034 | A | | 7/2008 | |
| CN | 101260126 | A | | 9/2008 | |
| CN | 102336786 | A | | 2/2012 | |
| CN | 105037449 | A | | 11/2015 | |
| CN | 106083942 | A | | 11/2016 | |
| CN | 111138502 | A | | 5/2020 | |
| WO | WO 2008/004246 | A1 | | 1/2008 | |

OTHER PUBLICATIONS

Wiemer et al., Human Reproduction, 1998, 13(4), p. 166-172. (Year: 1998).*
EPO English machine translation of CN 111138502 A, published May 12, 2020, [https://worldwide.espacenet.com/], accessed online on Dec. 15, 2025. (Year: 2020).*
EPO English machine translation of CN 102336786 A, published Feb. 1, 2012, [https://worldwide.espacenet.com/], accessed online on Dec. 15, 2025. (Year: 2012).*
Office Action for CN 202080002555.3 dated Mar. 7, 2022.
International Search Report for PCT/CN2020/119233 dated Jun. 24, 2021.

* cited by examiner

*Primary Examiner* — Jonathan S Lau
(74) *Attorney, Agent, or Firm* — Knobbe, Martens, Olson & Bear LLP

(57) ABSTRACT

Disclosed is a method for purifying sucralose, sequentially including: adding sucralose to ultrapure water, heating the resulting mixture for dissolution to obtain a dissolved solution, filtering the dissolved solution to obtain a filtrate, and then extracting the filtrate with an extraction solvent to remove non-polar impurities; subjecting the extracted recrystallization solution to concentration by evaporation to obtain a concentrated recrystallization solution with a preset concentration, and leaving the concentrated recrystallization solution to stand at a preset temperature for a preset time to produce a sucralose crystal nucleus in the concentrated recrystallization solution; subjecting the concentrated recrystallization solution containing the sucralose crystal nucleus to programmed cooling to obtain a recrystallization solution with a large amount of a sucralose crystal; and centrifuging the recrystallization solution with a large amount of a sucralose crystal to obtain a solid, and subjecting the solid to water-washing and drying to obtain a sucralose crystal.

12 Claims, 2 Drawing Sheets

METHOD FOR PURIFYING SUCRALOSE

CROSS REFERENCE TO RELATED APPLICATION

This application is a U.S. National Phase Application of PCT International Application Number PCT/CN2020/119233, filed on Sep. 30, 2020, designating the United States of America and published in the Chinese language. The disclosures of the above-referenced application are hereby expressly incorporated by reference in its entirety.

TECHNICAL FIELD

The present disclosure belongs to the field of manufacturing fine chemical products, and specifically relates to a method for purifying sucralose.

BACKGROUND ART

Sucralose is an artificial sweetener with high sweetness, excellent taste, and high safety, which has been widely used. Sucralose does not participate in human metabolism, and it is particularly interesting that sucralose is almost calorie-free, and thus could be provided to obese patients, diabetic patients, cardiovascular disease patients, and the elderly. In addition, sucralose has excellent chemical stability, is difficult to pyrolyse or hydrolyse, and exhibits prominent stability especially in an acidic solution. Sucralose will not cause caries and could contribute to dental health, and thus it could be used as a sweetener in oral care products such as toothpaste and mouthwash.

In a production process of sucralose, product purification is an important operating unit, because even a small amount of impurities could greatly affect the quality of the sucralose product. A main purpose of the product purification is to separate impurities and intermediate by-products from the sucralose product, such as monosaccharides, dichlorosucrose, sucralose isomers, tetrachlorosucrose, and esters, as well as a small or trace amount of catalyst and heavy metal residues. Currently, there are many reports on methods for purifying sucralose.

For example, U.S. Pat. No. 7,049,435 describes a purification method comprising: subjecting an aqueous solution of sucralose and impurities to extraction with a non-aromatic organic solvent insoluble in water to obtain an extraction phase and a first aqueous phase, such that a part of the impurities enter the extraction phase; and then subjecting the first aqueous phase to extraction with another organic solvent to obtain an organic phase and a second aqueous phase, such that sucralose enters the organic phase and impurities remain in the second aqueous phase to obtain pure sucralose.

For example, U.S. Pat. No. 5,498,709 describes a purification method comprising: subjecting an aqueous solution of sucralose to extraction with ethyl acetate, then removing residual dimethylformamide through water-washing, and finally crystallizing by concentration to obtain sucralose.

For example, U.S. Pat. No. 4,980,463 describes a purification method comprising: subjecting a sucralose mixture obtained after a deesterification reaction to extraction with an organic solvent to obtain an organic phase, then subjecting the organic phase to extraction with water to make sucralose enter an aqueous phase, and subjecting the aqueous phase to decolorization, concentration, and crystallization to obtain pure sucralose.

For example, Chinese Patent No. 101260126 describes a purification method comprising: adding a sucralose raw material or a concentrate thereof to a mixed solvent of an alcohol solvent and another solvent, heating the resulting mixture until the solid is completely dissolved, subjecting the resulting solution to a slow cooling for crystallization, standing, and separating to obtain a sucralose crystal.

For example, Chinese Patent No. 1639179 describes a purification method comprising: purifying a sucralose stock solution by a non-crystallization method such as extraction, chromatography, or distillation, then subjecting the resulting solution to continuous crystallization for three or more times, in which a mother liquor obtained from each crystallization is circulated to the previous crystallization, to obtain pure sucralose.

For example, Chinese Patent No. 101210034 describes a purification method comprising: adding crude sucralose to a mixed solvent including two solvents with much different boiling points to obtain a crude sucralose solution, wherein a solvent with a high boiling point exhibits small solubility for sucralose and a solvent with a low boiling point exhibits large solubility for sucralose; concentrating the crude sucralose solution under specified temperature and vacuum conditions, such that the solvent with a low boiling point volatilizes and sucralose remains in the solvent with a high boiling point to obtain a concentrated solution; and adding a small amount of pure sucralose to the concentrated solution, leaving to stand for crystallization until the crystallization is completed, and filtering the resulting solution to obtain a solid, drying the solid to obtain sucralose with a high purity.

The sucralose purification methods reported above are provided mainly for the purification of a crude material in a production process. Due to the influence of factors such as raw materials, circulating materials, purity of raw materials, process control, and quality requirements, sucralose products produced by these methods commonly have a low purity basically in a range of 90 wt % to 98 wt %, and only after multiple continuous crystallization, the purity could be increased to 98.0 wt % or more, wherein an ash (residue on ignition) content is in a range of 0.70 wt % to 0.10 wt % and a sodium acetate content is in a range of 50 ppm to 1,000 ppm. Although these conventional sucralose products meet the requirements in the Chinese National Standard "GB 25531-2010 *Food Additive Sucralose*", but they still could not meet the requirements of some high-end food, beverage, and drugs (purity: 99.5 wt % or more, residue on ignition: lower than 0.10 wt %, and sodium acetate content: 20 ppm or lower). It could also be known from the crystal data of the products that these sucralose products with insufficient purity generally have problems such as incomplete crystallization (weak spectral peak intensity) and complicated and diversified crystal forms (many impurity peaks), which will make the performance such as bulk density, flow speed, and storage time of the products fail to reach particularly ideal states. Therefore, a purification method that could rapidly and efficiently prepare a sucralose product with a high purity is urgently required to solve the above problems.

SUMMARY

In view of the above problems, the present disclosure provides a method for purifying sucralose which could overcome or at least partially solve the above problems.

According to an aspect of the present disclosure, provided is a method for purifying sucralose, sequentially including:

dissolution: adding sucralose to ultrapure water (UPW) to obtain a mixture, heating the mixture for dissolution to obtain a dissolved solution, and filtering the dissolved solution to obtain a recrystallization solution;

extraction: extracting the recrystallization solution with an extraction solvent to remove non-polar impurities, to obtain an extracted recrystallization solution;

nucleation: subjecting the extracted recrystallization solution to concentration by evaporation to obtain a concentrated recrystallization solution with a preset concentration, and leaving the concentrated recrystallization solution to stand at a preset temperature for a preset time to produce a sucralose crystal nucleus in the concentrated recrystallization solution;

crystallization: subjecting the concentrated recrystallization solution containing the sucralose crystal nucleus to gradient cooling to obtain a solution containing a large amount of a sucralose crystal; and collection: centrifuging the solution containing a large amount of a sucralose crystal to obtain a solid, and subjecting the solid to water-washing and drying to obtain a sucralose crystal.

According to another aspect of the present disclosure, provided is a sucralose crystal, which is prepared by the method described above, and has a purity of higher than 99.8%, a residue on ignition of lower than 0.20 wt %, and a moisture content of lower than 0.3 wt %.

The present disclosure has the following beneficial effects:

In the method for purifying sucralose according to the present disclosure, a sucralose crystal is prepared by first removing non-polar impurities through extraction, then promoting nucleation, and promoting the rapid growth of a crystal through a second-time nucleation procedure to ensure full crystallization. The prepared sucralose crystal has a high yield, a single crystal form, complete crystallization, a regular crystal morphology, a uniform crystal size, an extremely-high purity, an excellent color, a high bulk density, improved fluidity, and improved stability during long-term storage, and could meet the requirements of high-end products for sugar substitutes. In addition, the crystallization process takes a short time, which effectively shortens the production cycle of a product and reduces the production costs; and the crystallization process is controllable, involves mild conditions, and has low requirements for equipment, making the method very suitable for industrial production. Moreover, since the sucralose crystal product has a uniform crystal size and excellent solubility, no additional pretreatment is required before the sucralose crystal product is used, which simplifies the process flow.

The above description is merely a summary of the technical solutions of the present disclosure. In order to allow the technical means of the present disclosure to be understood clearly and implemented in accordance with the content of the specification and allow the above and other objectives, features, and advantages of the present disclosure to be obvious and easy to understand, specific embodiments of the present disclosure are described below.

BRIEF DESCRIPTION OF THE DRAWINGS

By reading the detailed description of the following preferred embodiments, various other advantages and benefits will become apparent to those of ordinary skill in the art. The accompanying drawings are provided merely to illustrate the preferred embodiments, rather than to limit the present disclosure. Throughout the accompanying drawings, the same reference numerals represent the same components. In the accompanying drawings.

DETAILED DESCRIPTION OF THE EMBODIMENTS

Figure 1:
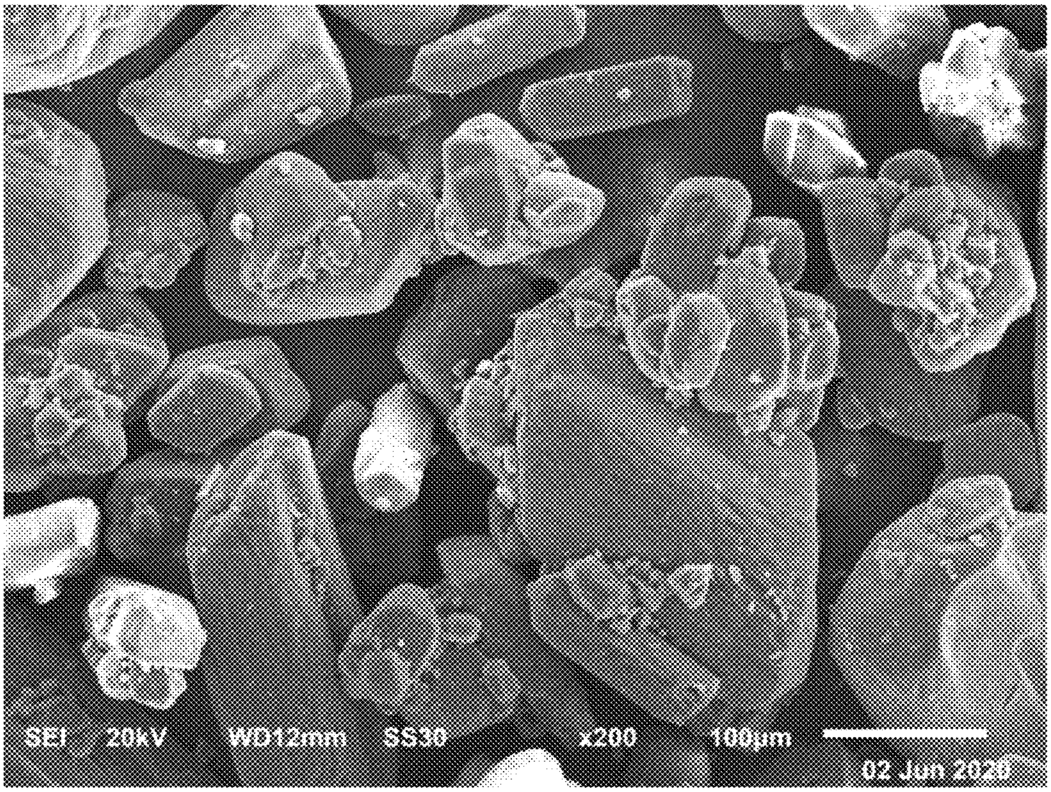
FIG. 1 shows a scanning electron microscopy (SEM) image of the sucralose crystal product prepared according to Example 1.

Exemplary embodiments of the present disclosure will be described in detail below with reference to the accompanying drawings. Although the accompanying drawings show exemplary embodiments of the present disclosure, it should be understood that the present disclosure may be implemented in various forms and should not be limited to the embodiments set forth herein. Instead, these embodiments are provided to make the present disclosure be understood thoroughly, and fully convey a scope of the present disclosure to those skilled in the art.

The concept of the present disclosure is as follows: In view of the problem that a sucralose product purified by the existing purification method has defects such as low purity, incomplete crystallization, complicated crystal form, irregular crystal morphology, and limited shelf time, the present disclosure provides a method for purifying sucralose which involves mild conditions and simple process and is conducted by extraction first and then two-step crystallization, such that the above problem is effectively avoided.

The method for purifying sucralose provided in the present disclosure sequentially includes:

Dissolution: sucralose is added to deionized water to obtain a mixture, and the mixture is heated for dissolution to obtain a dissolved solution, and the dissolved solution is filtered to obtain a recrystallization solution.

In the method for purifying sucralose provided in the present disclosure, the sucralose is first purified through extraction, and on the basis of this, recrystallization is conducted to remove various impurities in the sucralose crystal. The sucralose is first dissolved. Specifically, the sucralose is added to deionized water to obtain a mixture, and the mixture is heated for dissolution to obtain a dissolved solution, and then the dissolved solution is filtered to obtain a recrystallization solution. The filtering may be conducted with any filter in the prior art, and it is recommended to use a precision pipeline filter of more than 800 mesh.

Extraction: the recrystallization solution is extracted with an extraction solvent to remove non-polar impurities to obtain an extracted recrystallization solution.

Because sucralose has high polarity, the solubility of sucralose in water is much higher than the solubility of sucralose in some extraction solvents; and during the production of sucralose, many impurities will enter a final sucralose product, and these impurities are mostly low-polarity species. Therefore, treating a sucralose solution with an extraction solvent could selectively remove a variety of impurities, thereby achieving a good purification effect.

Nucleation: the extracted recrystallization solution is subjected to concentration by evaporation to obtain a concentrated recrystallization solution with a preset concentration, and the concentrated recrystallization solution is left to stand at a preset temperature for a preset time to produce a sucralose crystal nucleus in the concentrated recrystallization solution.

Crystallization: the concentrated recrystallization solution containing the sucralose crystal nucleus is subjected to gradient cooling to obtain a recrystallization solution containing a large amount of a sucralose crystal.

The nucleation and crystallization are the key steps in the method for purifying sucralose provided by the present disclosure. In the prior art, a crystal is generally directly produced in one step, and such crystal has many defects such as complicated crystal form, incomplete crystallization, irregular crystal morphology, low purity, and poor color. In the present disclosure, a crystal is produced by two-step crystallization, instead of the existing one-step crystallization: step 1, a sucralose crystal nucleus is first formed by controlling conditions; and step 2, gradient cooling is conducted on the formed crystal nucleus to rapidly form a large amount of a sucralose crystal.

Collection: the recrystallization solution containing a large amount of a sucralose crystal is centrifuged to obtain a solid, and the solid is washed with water and dried to obtain a sucralose crystal product.

After a large amount of a sucralose crystal is produced, the recrystallization solution is a suspension with the large amount of a sucralose crystal, and finally the sucralose crystal product is obtained by a collection step, specifically including, but not limited to, centrifugation, water-washing, and drying.

The method for purifying sucralose provided in the present disclosure sequentially includes: dissolution, extraction, nucleation, crystallization, and collection. For example, the extraction needs to be completed before the nucleation, by which organic impurities in the sucralose recrystallization mother liquor could be prevented from entering the final product. If the extraction is conducted after the nucleation, a part of the organic impurities will enter the crystal nucleus, and then will enter the final product, thereby adversely affecting the purity of the final product. For another example, the nucleation needs to be conducted before the crystallization, such that a seed crystal could be directly provided for the massive crystallization of sucralose, which could also shorten the time required for crystallization.

In the method for purifying sucralose provided by the present disclosure, extraction is conducted first to remove non-polar impurities, then nucleation is promoted, and the rapid growth of a crystal is promoted through a second-time nucleation procedure to ensure complete crystallization. The prepared sucralose crystal has a high yield, a single crystal form, complete crystallization, regular crystal morphology, a uniform crystal size, an extremely-high purity, an excellent color, a high bulk density, improved fluidity, and improved stability during long-term storage, and could meet the requirements of high-end products for sugar substitutes. In addition, the crystallization procedure takes a short time, which effectively shortens the production cycle of a product and reduces the production cost; and the crystallization procedure is controllable, involves mild conditions, and has low requirements for equipment, making it very suitable for industrial production. Moreover, since the sucralose crystal product has a uniform crystal size and excellent solubility, no additional pretreatment procedure is required before the sucralose crystal product is used, which simplifies the process flow.

Source and Performance of Crude Sucralose

In some embodiments of the present disclosure, the crude sucralose may be a commercially-available finished product or produced by any method in the prior art, including, but not limited to, monogroup-protected synthesis method, multigroup-protected synthesis method, and enzymatic catalysis method. Before the method of the present disclosure is implemented each time, the performance of crude sucralose is tested to facilitate the implementation of subsequent purification, and further, crude sucralose with performance falling within the following ranges may preferably be adopted to achieve a prominent purification effect.

In some embodiments of the present disclosure, the crude sucralose has an original purity of 98.0% to 99.6%; and in some other embodiments, the crude sucralose has an original purity of 99.0% to 99.5%. In some embodiments, the crude sucralose has a residue on ignition of 0.70 wt % to 0.10 wt %; and in some other embodiments, the crude sucralose has a residue on ignition of 0.20 wt % to 0.10 wt %.

The recrystallization method is such a process that is conducted by dissolving a crystal in a solvent or melting the crystal, and then crystallizing from the resulting solution or melt again. The recrystallization could purify an impure substance. The purification method provided in the present disclosure is a process for purifying a crude sucralose, and in order to obtain a sucralose crystal with excellent performance, the crude sucralose preferably have a relatively high original purity. In some embodiments, the crude sucralose has an original purity of 99.0% to 99.6%; and in some other embodiments, the crude sucralose has an original purity of 99.3% to 99.5%. In some embodiments, the crude sucralose has a residue on ignition of 0.70 wt % to 0.10 wt %; and in some other embodiments, the crude sucralose has a residue on ignition of 0.20 wt % to 0.10 wt %.

Performance and Amount of UPW

In some embodiments of the present disclosure, in the dissolution, UPW is used for dissolution. In some embodiments, it is recommended to use UPW as a solvent. UPW has a resistivity of greater than 18.0 MΩ·cm, and the closer the resistivity of UPW to 18.3 MΩ·cm, the better the effect.

In some embodiments of the present disclosure, there is no limitation on the amount of UPW, and based on a mass of sucralose, a ratio of a volume of UPW to the mass of sucralose may be in a range of 0.5 to 4.0 mL/g; and in some other embodiments, the ratio of the volume of UPW to the mass of sucralose may be in a range of 1.0 to 3.0 mL/g. If the volume of UPW is less than 50% of the mass of sucralose, indicating an under-use of UPW, it cannot completely dissolve the sucralose crude product and its impurities; and if the volume of UPW is more than 4.0 times the mass of sucralose, indicating an over-use of UPW, it not only causes unnecessary waste, but also increases the workload of subsequent evaporation and concentration and prolongs the overall process time.

Dissolution and Filtration Conditions

In some embodiments of the present disclosure, in the dissolution, the heating is conducted at a temperature of 25° C. to 50° C. for 10 min to 8 h, and in some other embodiments, the heating is conducted at a temperature of 35° C. to 45° C. for 20 min to 4 h; and the filtering is conducted with a precision pipeline filter of more than 800 mesh, and in some other embodiments, the filtering is conducted with a precision pipeline filter of more than 2,000 mesh.

In some embodiments of the present disclosure, there is no limitation on the conditions for the heating, and the heating may be conducted at 25° C. to 50° C. for 10 min to 8 h. The heating time and heating temperature could be determined according to the dissolution of the crude sucralose, which ensures the complete dissolution of the crude sucralose and does not cause unnecessary waste. In some other embodiments, the heating may be conducted at 35° C. to 45° C. for 20 min to 4 h.

After the dissolution of the crude sucralose, some solid impurities still could not be completely dissolved, which will adversely affect the subsequent growth of the crystal. Therefore, in some embodiments of the present disclosure, the dissolved solution obtained after the dissolution of the crude sucralose is filtered with a precision pipeline filter of more than 800 mesh. In some other embodiments, the dissolved solution obtained after the dissolution of the crude sucralose is filtered with a precision pipeline filter of more than 2,000 mesh.

Conditions and Degree of Extraction

In some embodiments of the present disclosure, in the extraction, an extraction solvent includes ethyl acetate or isopropyl acetate. A volume ratio of the extraction solvent to the recrystallization solution is in a range of 0.2 to 8.0, and preferably 1.0 to 4.0. If the volume of the extraction solvent is less than 20% of the volume of the recrystallization solution, indicating an under-use of the extraction solvent, low-polarity impurities in the sucralose solution could not be completely removed; and if the volume of the extraction solvent is more than 8.0 times the volume of the recrystallization solution, indicating an over-use of the extraction solvent, it will cause unnecessary waste, increase the workload of subsequent distillation for solvent recovery, and extends the time of the overall process.

For the specific means of the extraction, the present disclosure recommends the use of a continuous countercurrent extraction technique or other high-efficiency extraction technique such as a forced extraction technique and a countercurrent centrifugal extraction technique, which could achieve an effect equivalent to a multiple extraction effect (10 times or more) at a small amount. After the extraction is completed, a resulting system is allowed to stand for a long time or centrifuged for separation, thereby achieving a prominent extraction and separation effect. In some embodiments of the present disclosure, a centrifugal countercurrent extraction device is adopted, which has a prominent extraction and separation effect.

Conditions and Degree of Concentration

In some embodiments of the present disclosure, in the nucleation, the concentration by evaporation is conducted at a temperature of 45° C. to 60° C. and a pressure of −95 kPa to −101 kPa for 10 min to 12 h; and the preset concentration is in a range of 60 wt % to 80 wt %.

In the present disclosure, there is no limitation on the means of the concentration. In some embodiments of the present disclosure, the concentration may be conducted by vacuum distillation or rotary distillation, and the concentration may be conducted at a temperature of 45° C. to 60° C. and a pressure of −95 kPa to −101 kPa for 10 min to 12 h. If the temperature of the concentration is lower than 45° C., indicating an over-low temperature, the efficiency of solvent evaporation will be too low and the concentration time will be too long; and if the concentration temperature is higher than 60° C., indicating an over-high temperature, the solvent will evaporate too quickly and it is difficult to control the evaporation near a concentration end point. If the pressure of the concentration is lower than −101 kPa, indicating an over-low reduced pressure, the solvent will evaporate too quickly, and it poses high requirements on equipment, which increases the equipment cost; and if the pressure of the concentration is higher than −95 kPa, indicating an over-high reduced pressure, the concentration effect will be poor, and the solvent evaporation time will be long, which increases the time cost.

When the recrystallization solution is concentrated to a specified degree, the distillation is stopped. The concentration endpoint refers to concentrating the recrystallization solution to a preset concentration, and the preset concentration refers to a mass concentration of a solute, based on a total mass of the solution. In some embodiments of the present disclosure, there is no limitation on the preset concentration, and the preset concentration is recommended to be in a range of 60 wt % to 80 wt %, in other words, a mass of water in the solution is 20 wt % to 40 wt % of the solution. If the preset concentration of the recrystallization solution is lower than 60 wt %, indicating an over-use solvent, it is difficult to produce crystal nucleus in the subsequent nucleation; and if the preset concentration of the recrystallization solution is higher than 80 wt %, indicating an under-use solvent, during a temperature-holding procedure of the subsequent nucleation, the solvent rapidly and completely evaporates and the nucleation and the crystallization could not be effectively separated, resulting in a large amount of irregular crystal and even failure of the entire purification procedure.

Process Parameters of Nucleation

In some embodiments of the present disclosure, in the nucleation, the preset temperature is in a range of 50° C. to 60° C., and the preset time is in a range of 0.5 h to 3 h. And in some other embodiments, the preset temperature is in a range of 52° C. to 58° C., and the preset time is in a range of 0.5 h to 2 h.

In the nucleation, the holding temperature (i.e., the preset temperature) and the holding time (i.e., the preset time) are important parameters to promote the nucleation, and without proper control, the crystal nucleus could not be effectively produced. In some embodiments, the preset temperature is in a range of 50° C. to 60° C., and the preset time is in a range of 0.5 h to 3 h. In some other embodiments, the preset temperature is in a range of 52° C. to 58° C., and the preset time is in a range of 0.5 h to 2 h. If the preset temperature is lower than 50° C., indicating an over-low temperature, the crystal nucleus will grow too fast, resulting in crystal precipitation; and if the preset temperature is higher than 60° C., indicating an over-high temperature, the crystal nucleus will grow too slowly, and the crystal nucleus of a small amount will adversely affect the subsequent crystal growth. The setting of the holding time also requires a lot of investigation. If the holding time is shorter than 0.5 h, indicating an over-short time of the nucleation, the crystal nucleus will grow too slowly, and a small amount of the crystal nucleus adversely affects the subsequent crystal growth; and if the holding time is longer than 2 h, indicating an over-long time, a large amount of the crystal nucleus will be formed and the subsequent crystal growth will be insufficient, resulting in a small crystal size.

Process Parameters of Crystallization

In some embodiments of the present disclosure, in the crystallization, the gradient cooling is conducted as follows: cooling the concentrated recrystallization solution containing the sucralose crystal nucleus from a first temperature of 52° C. to 58° C. to a second temperature of 43° C. to 47° C. at a first cooling rate of 1° C./10 min to 1° C./60 min, and holding at the second temperature for 0.5 h to 3 h, and further cooling the concentrated recrystallization solution containing the sucralose crystal nucleus to a third temperature of 18° C. to 22° C. at a second cooling rate of 1° C./10 min to 1° C./60 min. In some other embodiments, the gradient cooling is conducted as follows: cooling the concentrated recrystallization solution containing the sucralose crystal nucleus from a first temperature of 52° C. to 58° C. to a second temperature of 45° C. at a first cooling rate of 1° C./10 min to 1° C./60 min, and holding at the second temperature for 0.5 h to 3 h, and further cooling the concentrated recrystallization solution containing the sucralose crystal nucleus to a third temperature of 20° C. at a second cooling rate of 1° C./10 min to 1° C./60 min.

The crystallization is an important part of the recrystallization method provided in the present disclosure, and in the present disclosure, gradient cooling is conducted in the present of the crystal nucleus, such that sucralose is precipitated from the solution and grows on the crystal nucleus to rapidly form a large amount of a crystal of a regular and single crystal form. In some embodiments, the gradient cooling is conducted as follows: cooling the concentrated recrystallization solution containing the sucralose crystal nucleus from a first temperature of 52° C. to 58° C. to a second temperature of 43° C. to 47° C. at a first cooling rate of 1° C./10 min to 1° C./60 min, and holding at the second temperature for 0.5 h to 3 h, and further cooling the concentrated recrystallization solution containing the sucralose crystal nucleus to a third temperature of 18° C. to 22° C. at a second cooling rate of 1° C./10 min to 1° C./60 min. In some other embodiments, the gradient cooling is conducted as follows: cooling the concentrated recrystallization solution containing the sucralose crystal nucleus from a first temperature of 52° C. to 58° C. to a second temperature of 45° C. at a first cooling rate of 1° C./10 min to 1° C./60 min, and holding at the second temperature for 0.5 h to 3 h, and further cooling the concentrated recrystallization solution containing the sucralose crystal nucleus to a third temperature of 20° C. at a second cooling rate of 1° C./10 min to 60 min.

The gradient cooling starts from the first temperature of 52° C. to 58° C., which means that at the end of the nucleation, the temperature of the solution as a whole shall be controlled in a range of 52° C. to 58° C. to facilitate the smooth progress of the crystallization.

After the solution is cooled to the second temperature of 43° C. to 47° C. at a first cooling rate of 1° C./10 min to 1° C./60 min and held at the second temperature for 0.5 h to 3 h, a small amount of crystal grows and is precipitated, and the crystal nucleus could promote the crystal growth and provide a seed crystal for the crystal growth. After the holding is completed, the solution is further cooled to a third temperature of 18° C. to 22° C. at a second cooling rate of 1° C./10 min to 1° C./60 min, during which the crystal grows rapidly in a large quantity; and after the cooling is completed, that is, when the gradient cooling reaches the endpoint, the crystal growth is completed, at which point sucralose in the solution is mostly crystallized and precipitated.

Subsequently, conventional centrifugation, water-washing, and drying are conducted. That is, the solution with a large amount of a sucralose crystal is subjected to solid-liquid separation, and the resulting wet sucralose crystal is washed with a small amount of UPW and then dried to obtain a sucralose crystal with a high purity and a single crystal form.

The sucralose crystal prepared by any method for purifying sucralose provided in the present disclosure has a purity of greater than 99.8%, a residue on ignition of less than 0.10 wt %, and a moisture content of less than 0.3 wt %, wherein the sucralose crystal has a triclinic crystal form ($C_{2/C}$ crystal system), and the strongest spectral peaks of the sucralose crystal on an XRD pattern are at 16.7±0.2°, 21.1±0.2°, 24.5±0.2°, 24.9±0.2°, 29.5±0.2°, and 40.6±0.2°, respectively.

Testing Methods Involved in the Present Disclosure

The test methods used in examples and comparative examples of the present disclosure are described below, and will not be repeated in each example.

A test and analysis method for the purity of sucralose involved in the present disclosure could refer to the Chinese National Standard "GB25531-2010 *for Food Additive Sucralose*".

Analysis and determination conditions of the purity of sucralose: High-performance liquid chromatograph from Shimadzu, Japan: RID-10A differential refractive index detector, LC-10ADVP high-pressure pump, and CTO-10ASVP incubator; chromatographic column: Agilent XDB C18 column (250 mm×4.6 mm, 5 μm); mobile phase: methanol-0.125% dipotassium phosphate (DKP) aqueous solution (4:6); column temperature: 30° C.; and flow rate: 1.0 mL/min. Methanol (chromatographically pure), DKP (analytically pure), UPW, and sucralose (purity: 99.9%) are required, and a content is determined by an external standard method.

The determination and analysis method of an acetic acid content is the same as that of sucralose, which will not be repeated herein.

The method or conditions for determining an impurity content (residue on ignition) could refer to the Chinese National Standard GB/T 7531-1987: Determination of Ash for Organic Chemical Products.

Test conditions of XRD: X-ray diffractometer with a model of Bruker B 8Advance, which adopts Kα1 rays of a Cu target with a wavelength of 1.5418 nm.

Test conditions of SEM: Japanese JSM-65-10 scanning electron microscope.

The method and conditions for determining a moisture content can refer to the Chinese National Standard GB/T 6283-2008: Chemical products-Determination of Water Karl Fischer Method (General Method).

Determination method of bulk density: A sample of an example is added to a 50 mL measuring cylinder and continuously subjected to free-fall impact at a height of 5 cm until the sample is compacted, and then a mass of the sample is measured to obtain bulk density data.

Example 1

100 g of crude sucralose (with a purity of 99.48%, an impurity content (residue on ignition) of 0.21 wt %, and a sodium acetate content of 500 ppm) was taken and added to 100 mL of UPW to obtain a mixture. The mixture was heated to 50° C. and stirred for 30 min for dissolution to obtain a sucralose solution. The sucralose solution was filtered through a precision pipeline filter (2,000 mesh) for purification, then subjected to countercurrent extraction with 200 mL of isopropyl acetate for 1 h, left to stand and subjected to liquid separation to obtain an aqueous phase. The aqueous phase was subjected to vacuum concentration at a temperature of 60° C. and a pressure of −100 kPa for 30 min to obtain a concentrated recrystallization solution of sucralose with a solid content of about 60 wt % (namely, a moisture content of about 40 wt %).

The concentrated recrystallization solution of sucralose was held at 60° C. for 1 h to produce an effective crystal nucleus, then cooled to 45° C. at a first cooling rate of 1° C./20 min and held at 45° C. for 2 h, and then further cooled to 20° C. at a second cooling rate of 1° C./20 min to obtain a large amount of a sucralose crystal in the concentrated recrystallization solution. The concentrated recrystallization solution containing a large amount of a sucralose crystal was centrifuged to obtain a wet sucralose crystal. The wet sucralose crystal was washed with a small amount of cold UPW and dried to obtain 70 g of a sucralose crystal with a high purity, which had a purity of 99.98%, an impurity content (residue on ignition) of 0.08 wt %, a sodium acetate content of 10 ppm, and a moisture content of 0.2 wt %.

Figure 3:
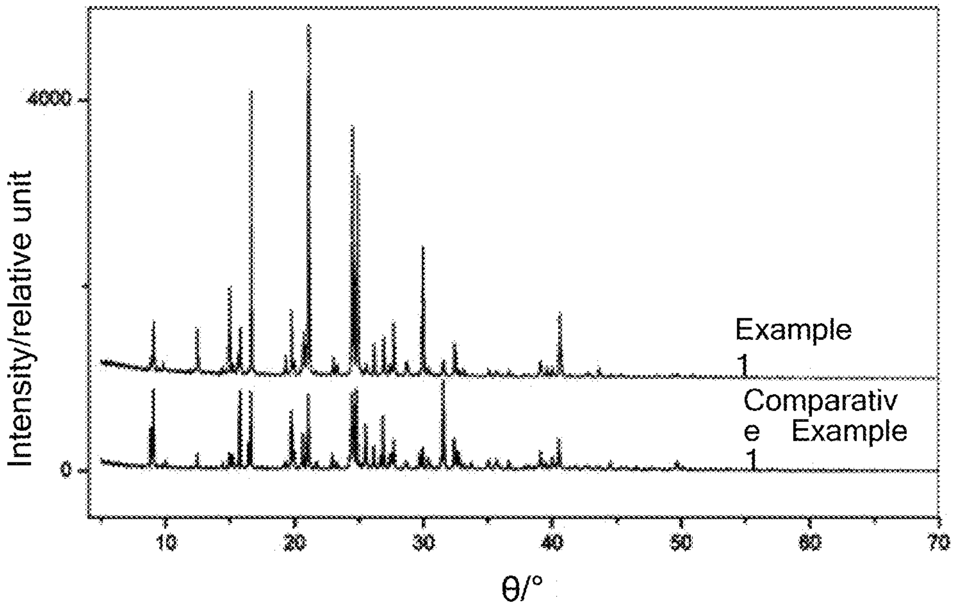
FIG. 3 shows X-ray diffraction (XRD) patterns of the sucralose crystal products prepared according to Example 1 and Comparative Example 1.

An SEM image of the sucralose crystal is shown in FIG. 1; and an XRD pattern of the sucralose crystal is shown in FIG. 3. It can be seen from FIG. 1 that the sucralose crystal obtained by the method of this example has a typical triclinic crystal structure corresponding to a $C_{2/C}$ crystal system, which has a small size variation range, excellent uniformity, and a simple crystal form.

Example 2

100 g of crude sucralose (with a purity of 99.48%, an impurity content (residue on ignition) of 0.21 wt %, and a sodium acetate content of 500 ppm) was taken and added to 100 mL of UPW to obtain a mixture. The mixture was heated to 35° C. and stirred for 60 min for dissolution to obtain a sucralose solution. The sucralose solution was filtered through a precision pipeline filter (800 mesh) for purification, then subjected to countercurrent extraction with 200 mL of ethyl acetate for 0.5 h, left to stand and subjected to liquid separation to obtain an aqueous phase. The aqueous phase was subjected to vacuum concentration at a temperature of 55° C. and a pressure of −95 kPa for 2 h to obtain a concentrated recrystallization solution of sucralose with a solid content of 70 wt % (namely, a moisture content of 30 wt %).

The concentrated recrystallization solution of sucralose was held at 55° C. for 1 h to produce an effective crystal nucleus, then cooled to 45° C. at a first cooling rate of 1° C./20 min and held at 45° C. for 2 h, and then cooled to 20° C. at a second cooling rate of 1° C./20 min to obtain a large amount of a sucralose crystal in the concentrated recrystallization solution. The concentrated recrystallization solution containing a large amount of a sucralose crystal was centrifuged to obtain a wet sucralose crystal. The wet sucralose crystal was washed with a small amount of cold UPW and dried to obtain 75 g of a sucralose crystal with a high purity, which had a purity of 99.69%, an impurity content (residue on ignition) of 0.09 wt %, a sodium acetate content of 18 ppm, and a moisture content of 0.2 wt %.

Example 3

100 g of crude sucralose (with a purity of 99.48%, an impurity content (residue on ignition) of 0.21 wt %, and a sodium acetate content of 500 ppm) was taken and added to 60 mL of UPW to obtain a mixture. The mixture was heated to 50° C. and stirred for 30 min for dissolution to obtain a sucralose solution. The sucralose solution was filtered through a precision pipeline filter (800 mesh) for purification, then subjected to countercurrent extraction with 100 mL of ethyl acetate for 0.5 h, left to stand, and subjected to liquid separation to obtain an aqueous phase. The aqueous phase was subjected to vacuum concentration at a temperature of 60° C. and a pressure of −95 kPa for 2 h to obtain a concentrated recrystallization solution of sucralose with a solid content of 70 wt % (namely, a moisture content of 30 wt %).

The concentrated recrystallization solution of sucralose was held at 55° C. for 0.5 h to produce an effective crystal nucleus, then cooled to 46° C. at a first cooling rate of 1° C./20 min and held at 46° C. for 1 h, and then cooled to 19° C. at a second cooling rate of 1° C./20 min to obtain a large amount of a sucralose crystal in the concentrated recrystallization solution. The concentrated recrystallization solution containing a large amount of a sucralose crystal was centrifuged to obtain a wet sucralose crystal. The wet sucralose crystal was washed with a small amount of cold UPW and dried to obtain 68 g of a sucralose crystal with a high purity, which had a purity of 99.68%, an impurity content (residue on ignition) of 0.10 wt %, a sodium acetate content of 20 ppm, and a moisture content of 0.2 wt %.

Example 4

100 g of crude sucralose (with a purity of 99.48%, an impurity content (residue on ignition) of 0.11 wt %, and a sodium acetate content of 500 ppm) was taken and added to 200 mL of UPW to obtain a mixture. The mixture was heated to 40° C. and stirred for 30 min for dissolution to obtain a sucralose solution. The sucralose solution was filtered through a precision pipeline filter (800 mesh) for purification, then subjected to countercurrent extraction with 200 mL of ethyl acetate for 0.5 h, left to stand, and subjected to liquid separation to obtain an aqueous phase. The aqueous phase was subjected to vacuum concentration at a temperature of 55° C. and a pressure of −101 kPa for 30 min to obtain a concentrated recrystallization solution of sucralose with a solid content of 60 wt % (namely, a moisture content of 40 wt %).

The concentrated recrystallization solution of sucralose was held at 55° C. for 1 h to produce an effective crystal nucleus, then cooled to 44° C. at a first cooling rate of 1° C./30 min and held at 44° C. for 2 h, and then cooled to 21° C. at a second cooling rate of 1° C./30 min to obtain a large amount of a sucralose crystal in the concentrated recrystallization solution. The concentrated recrystallization solution containing a large amount of a sucralose crystal was centrifuged to obtain a wet sucralose crystal. The wet sucralose crystal was washed with a small amount of cold UPW and dried to obtain 72 g of a sucralose crystal with a high purity, which had a purity of 99.99%, an impurity content (residue on ignition) of 0.07 wt %, a sodium acetate content of 8 ppm, and a moisture content of 0.2 wt %.

Example 5

100 g of crude sucralose (with a purity of 99.48%, an impurity content (residue on ignition) of 0.11 wt %, and a sodium acetate content of 500 ppm) was taken and added to 200 mL of UPW to obtain a mixture. The mixture was heated to 40° C. and stirred for 30 min for dissolution to obtain a sucralose solution. The sucralose solution was filtered through a precision pipeline filter (800 mesh) for purification, then subjected to countercurrent extraction with 200 mL of isopropyl acetate for 0.5 h, left to stand; and subjected to liquid separation to obtain an aqueous phase. The aqueous phase was subjected to vacuum concentration at a temperature of 55° C. and a pressure of −95 kPa for 2 h to obtain a concentrated recrystallization solution with a solid content of 60 wt % (namely, a moisture content of 40 wt %).

The concentrated recrystallization solution of sucralose was held at 55° C. for 1 h to produce an effective crystal nucleus, then cooled to 44° C. at a first cooling rate of 1° C./30 min and held at 44° C. for 2 h, and then cooled to 21° C. at a second cooling rate of 1° C./30 min to obtain a large amount of a sucralose crystal in the concentrated recrystallization solution. The concentrated recrystallization solution containing a large amount of a sucralose crystal was centrifuged to obtain a wet sucralose crystal. The wet sucralose crystal was washed with a small amount of cold UPW and dried to obtain 73 g of a sucralose crystal with a high purity, which had a purity of 99.87%, an impurity content (residue on ignition) of 0.09 wt %, a sodium acetate content of 12 ppm, and a moisture content of 0.2 wt %.

Example 6

100 g of crude sucralose (with a purity 99.48%, an impurity content (residue on ignition) of 0.11 wt %, and a sodium acetate content of 500 ppm) was taken and added to 200 mL of UPW to obtain mixture. The mixture was heated to 40° C. and stirred for 30 min for dissolution to obtain a sucralose solution. The sucralose solution was filtered through a precision pipeline filter (800 mesh) for purification, then subjected to countercurrent extraction with 100 mL of isopropyl acetate for 0.5 h, left to stand; and subjected to liquid separation to obtain an aqueous phase. The aqueous phase was subjected to vacuum concentration at a temperature of 55° C. and a pressure of −95 kPa for 2 h to obtain a concentrated recrystallization solution of sucralose with a solid content of 60 wt % (namely, a moisture content of 40 wt %).

The concentrated recrystallization solution of sucralose was held at 55° C. for 1 h to produce an effective crystal nucleus, then cooled to 44° C. at a first cooling rate of 1° C./30 min and held at 44° C. for 2 h, and then cooled to 21° C. at a second cooling rate of 1° C./30 min to obtain a large amount of a sucralose crystal in the concentrated recrystallization solution. The concentrated recrystallization solution containing a sucralose crystal was centrifuged to obtain a wet sucralose crystal. The wet sucralose crystal was washed with a small amount of cold UPW and dried to obtain 76 g of a sucralose crystal with a high purity, which had a purity of 99.78%, an impurity content (residue on ignition) of 0.09 wt %, a sodium acetate content of 13 ppm, and a moisture content of 0.2 wt %.

Comparative Example 1

100 g of crude sucralose (with a purity of 99.48%, an impurity content (residue on ignition) of 0.21 wt %, and a sodium acetate content of 500 ppm) was taken and added to 100 mL of UPW to obtain a mixture. The mixture was heated to 50° C. and stirred for 30 min to obtain a sucralose solution. The sucralose solution was filtered through a precision pipeline filter (2,000 mesh) for purification and then subjected to vacuum concentration at a temperature of 60° C. and a pressure of −100 kPa for 30 min to obtain a concentrated recrystallization solution of sucralose with a solid content of about 60 wt % (namely, a moisture content of about 40 wt %).

The concentrated recrystallization solution of sucralose was cooled down to 20° C. at a cooling rate of 1° C./20 min to obtain a large amount of a sucralose crystal in the concentrated recrystallization solution. The concentrated recrystallization solution containing a large amount of a sucralose crystal was centrifuged to obtain a wet sucralose crystal, and the wet sucralose crystal was washed with a small amount of cold UPW and dried to obtain 72 g of a sucralose crystal with a high purity, which had a purity of 99.66%, an impurity content (residue on ignition) of 0.15 wt %, a sodium acetate content of 25 ppm, and a moisture content of 0.2 wt %.

Figure 2:
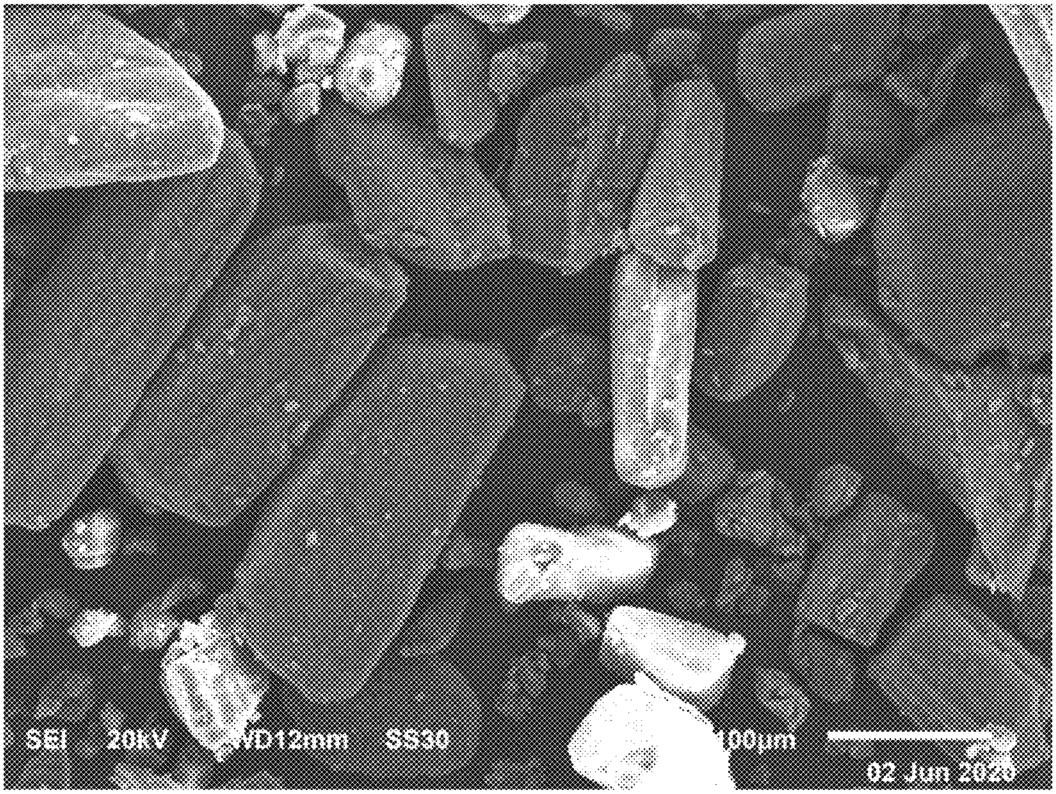
FIG. 2 shows an SEM image of the sucralose crystal product prepared according to Comparative Example 1.

An SEM image of the sucralose crystal obtained in Comparative Example 1 is shown in FIG. 2; and an XRD pattern of the sucralose crystal is shown in FIG. 3. It can be seen from FIG. 1 and FIG. 2 that the sucralose crystals obtained according to Example 1 and Comparative Example 1 are significantly different in terms of the crystal form and structure. FIG. 2 shows an SEM image of the sucralose crystal prepared according to Comparative Example 1, and FIG. 1 shows an SEM image of the sucralose crystal prepared according to Example 1. It can be seen from the comparison of the two images that the sucralose crystal obtained according to Comparative Example 1 shown in FIG. 2 has a typical orthorhombic crystal structure corresponding to the $P_{1/2}$ crystal system reported in the prior art, and the sucralose crystal obtained according to Example 1 shown in FIG. 1 has a typical triclinic crystal structure corresponding to the $C_{2/C}$ crystal system reported in the prior art. In addition, the sucralose crystal shown in FIG. 2 has a large difference in size and poor uniformity, also includes a small amount of triclinic crystal, and has a complicated crystal form, and the sucralose crystal shown in FIG. 1 has a small difference in size, excellent uniformity, and a simple crystal form.

FIG. 3 shows XRD patterns of the sucralose crystals obtained according to Comparative Example 1 and Example 1. It can be seen from FIG. 3 that: first, the peak intensity of the XRD of the sucralose crystal obtained according to Example 1 is 4 to 5 times that corresponding to the sucralose crystal obtained according to Comparative Example 1, indicating that the sucralose crystal obtained according to Example 1 has a more complete and simpler crystal form than the sucralose crystal obtained according to Comparative Example 1; and second, the XRD pattern of the sucralose crystal obtained according to Example 1 is quite different from the XRD pattern of the sucralose crystal obtained according to Comparative Example 1, which is consistent with the conclusions from the above SEM images of the crystals. Furthermore, the strongest spectral peaks of the sucralose crystal obtained according to Example 1 are significantly different from the strongest spectral peaks of the sucralose crystal obtained according to Comparative Example 1, wherein the strongest spectral peaks of the sucralose crystal obtained according to Example 1 are at the following positions: 16.7±0.2°, 21.1±0.2°, 24.5±0.2°, 24.9±0.2°, 29.5±0.2°, and 40.6±0.2°, and the strongest spectral peaks of the sucralose crystal obtained according to Comparative Example 1 are at the following positions: 8.8±0.2°, 9.0±0.2°, 15.7±0.2°, 16.6±0.2°, 21.0±0.2°, 24.5±0.2°, 24.8±0.2°, and 31.5±0.2°; and the strongest spectral peaks presented both in the XRD patterns of the sucralose crystals obtained according to Example 1 and Comparative Example 1 are at the following positions: 16.7±0.2°, 21.1±0.2°, 24.5±0.2°, and 24.9±0.2°, indicating that, the crystal structure of Comparative Example 1 includes the same crystal form as in the crystal structure of Example 1, but also includes other strongest spectral peaks at positions of: 8.8±0.2°, 9.0±0.2°, 24.8±0.2°, and 31.5±0.2°, indicating that the crystal structure of Comparative Example 1 includes other crystal forms, that is, the sucralose prepared according to Comparative Example 1 has a mixed crystal form.

Comparative Example 2

100 g of crude sucralose (with a purity of 99.48%, an impurity content (residue on ignition) of 0.21 wt %, and a sodium acetate content of 500 ppm) was taken and added to 100 mL of UPW to obtain a mixture. The mixture was heated to 50° C. and stirred for 30 min to obtain a sucralose solution. The sucralose solution was filtered through a precision pipeline filter (2,000 mesh) for purification and then subjected to vacuum concentration at a temperature of 60° C. and a pressure of −100 kPa for 30 min to obtain a concentrated recrystallization solution of sucralose with a solid content of about 60 wt % (namely, a moisture content of about 40 wt %).

The concentrated recrystallization solution of sucralose was held at 60° C. for 1 h to produce an effective crystal nucleus, then cooled to 45° C. at a first cooling rate of 1° C./20 min and held at 45° C. for 2 h, and then further cooled to 20° C. at a second cooling rate of 1° C./20 min to obtain a large amount of a sucralose crystal in the concentrated recrystallization solution. The concentrated recrystallization containing a sucralose crystal was centrifuged to obtain a wet sucralose crystal. The wet sucralose crystal was washed with a small amount of cold UPW and dried to obtain 73 g of a sucralose crystal with a high purity, which had a purity of 99.76%, an impurity content (residue on ignition) of 0.15 wt %, a sodium acetate content of 15 ppm, and a moisture content of 0.2 wt %.

Comparative Example 3

100 g of crude sucralose (with a purity of 99.48%, an impurity content (residue on ignition) of 0.21 wt %, and a sodium acetate content of 500 ppm) was taken and added to 100 mL of UPW to obtain a mixture. The mixture was heated to 50° C. and stirred for 30 min to obtain a sucralose solution. The sucralose solution was filtered through a precision pipeline filter (2,000 mesh) for purification, then subjected to countercurrent extraction with 200 mL of isopropyl acetate for 1 h, left to stand and subjected to liquid separation to obtain an aqueous phase. The aqueous phase was subjected to vacuum concentration at a temperature of 60° C. and a pressure of −100 kPa for 30 min to obtain a concentrated recrystallization solution of sucralose with a solid content of about 60 wt % (namely, a moisture content of about 40 wt %).

The concentrated recrystallization solution of sucralose was cooled from 60° C. to 20° C. at a cooling rate of 1° C./20 min to obtain a large amount of a sucralose crystal in the concentrated recrystallization solution. The concentrated recrystallization solution containing a sucralose crystal was centrifuged to obtain a wet sucralose crystal. The wet sucralose crystal was washed with a small amount of cold UPW and dried to obtain 71 g of a sucralose crystal with a high purity, which had a purity of 99.68%, an impurity content (residue on ignition) of 0.11 wt %, a sodium acetate content of 27 ppm, and a moisture content of 0.2 wt %.

In order to visually compare the technical effects of Examples 1 to 6 and Comparative Examples 1 to 3, the performance of sucralose purified according to Examples 1 to 6 and Comparative Examples 1 to 3 is shown in Table 1.

Example 7

The products obtained according to Examples 1 to 6 and Comparative Examples 1 to 3 each were subjected to an accelerated stability test.

In accordance with The International Council for Harmonisation of Technical Requirements for Pharmaceuticals for Human Use (ICH) Harmonised Tripartite Guideline on "Stability Testing of New Drug Substances and Products", the crystal products and raw material products of the present disclosure each were subjected to a stability test, and test results show that the crystal products and raw material products have passed the stability test. Detailed experimental data is shown in Table 1 below.

TABLE 1

Accelerated stability test results of Examples 1 to 6 and Comparative Examples 1 to 3

| Sample | Raw material | Example 1 | Example 2 | Example 3 | Example 4 | Example 5 | Example 6 | Comparative Example 1 | Comparative Example 2 | Comparative Example 3 |
|---|---|---|---|---|---|---|---|---|---|---|
| Purity, % | 99.48 | 99.98 | 99.69 | 99.68 | 99.99 | 99.87 | 99.78 | 99.66 | 99.76 | 99.68 |
| Residue on ignition, % | 0.21 | 0.08 | 0.09 | 0.10 | 0.07 | 0.09 | 0.09 | 0.15 | 0.15 | 0.11 |
| Sodium acetate content, ppm | 500 | 10 | 18 | 20 | 8 | 12 | 13 | 25 | 15 | 27 |
| Moisture content, % | 0.3 | 0.2 | 0.2 | 0.2 | 0.2 | 0.2 | 0.2 | 0.2 | 0.2 | 0.2 |
| Bulk density, g/mL | 0.978 | 1.109 | 1.056 | 1.067 | 1.110 | 1.103 | 10.085 | 0.981 | 1.021 | 0.979 |
| Production (g) | / | 70 | 75 | 68 | 72 | 73 | 76 | 72 | 73 | 71 |
| Yield (%) | / | 0.70 | 0.75 | 0.68 | 0.72 | 0.73 | 0.76 | 0.72 | 0.73 | 0.71 |
| One month (%) | 99.36 | 99.95 | 99.65 | 99.63 | 99.94 | 99.85 | 99.74 | 99.61 | 99.73 | 99.63 |
| Three months (%) | 99.12 | 99.92 | 99.59 | 99.56 | 99.91 | 99.79 | 99.70 | 99.57 | 99.69 | 99.58 |
| Six months (%) | 99.05 | 99.87 | 99.50 | 99.47 | 99.85 | 99.73 | 99.63 | 99.51 | 99.63 | 99.50 |
| Twelve months (%) | 98.78 | 99.79 | 99.33 | 99.26 | 99.73 | 99.60 | 99.51 | 99.38 | 99.47 | 99.35 |
| Twenty-four months (%) | 98.42 | 99.56 | 98.98 | 98.87 | 99.69 | 99.35 | 99.23 | 99.12 | 99.20 | 99.04 |

Note:
Storage conditions are as follows: temperature: 40° C. ± 2° C., and relative humidity: 60% RH ± 5% RH.

It can be seen from Table 1 that the products in Examples 1 to 6 each have an impurity content (residue on ignition) of lower than 0.10 wt %, while the products in Comparative Examples 1 to 3 each have an impurity content (residue on ignition) of 0.11 wt % to 0.15 wt %; and the products in Examples 1 to 6 each have a sodium acetate content of 20 ppm or less, while the products in Comparative Examples 1 and 3 each have a sodium acetate content of more than 20 ppm. Compared with the examples, in Comparative Example 2, only the extraction is omitted, and the extraction has no influence on the sodium acetate content. Therefore, the product in Comparative Example 2 also has a sodium acetate content of 20 ppm or less. In summary, the sucralose obtained by the purification method according to the present disclosure could meet the strict requirements of high-quality sugar substitutes; and the sucralose obtained according to Comparative Examples 1 to 3 could not meet the requirements.

The sucralose products in Comparative Examples 1 to 3 each have an purity of 99.66% to 99.76%; and the sucralose product in Example 1 has an impurity as high as 99.98% and the sucralose product in Example 4 has an impurity of up to 99.99%. Therefore, the purification method of the present disclosure could be used to produce sucralose of extremely high purity.

It can also be seen from the storage stability data from one month to twenty-four months in Table 1 that the storage stability of sucralose is not only related to the purity of the sucralose, but also related to the residue on ignition and sodium acetate content in the sucralose; and the higher the purity and the lower the residue on ignition and sodium acetate content, the higher the storage stability of sucralose.

In addition, it can also be seen from the bulk density data in Table 1 that the bulk density data is also related to the purity of a sample, indicating that, with the optimization of the purity and crystal structure of a sample, the sucralose crystal system changes from a chaotic orthorhombic crystal system to a single triclinic crystal system and changes from a rod-like crystal structure to a triclinic structure, which leads to an increase in the bulk density. It means that increased samples could be accommodated by packaging of the same volume, which could significantly improve the transportation efficiency. In addition, the triclinic crystal structure has higher fluidity than the rod-like crystal structure, which will benefit the pipeline transportation and automated production to some extent.

In summary, in the purification method of sucralose with a high purity provided by the present disclosure, the sucralose crystal is obtained by first removing non-polar impurities through extraction, then promoting nucleation, and promoting the rapid growth of a crystal through a second-time nucleation procedure to ensure full crystallization; and the prepared sucralose crystal has a high yield, a single crystal form, complete crystallization, a regular crystal morphology, a uniform crystal size, an extremely-high purity, an excellent color, a high bulk density, improved fluidity, and improved stability during long-term storage, and could meet the requirements of high-end products for sugar substitutes. In addition, the crystallization procedure takes a short time, which effectively shortens the production cycle of a product and reduces the production cost; and the crystallization procedure is controllable, involves mild conditions, and has low requirements for equipment, which is very suitable for industrial production. Moreover, since the sucralose crystal product has a uniform crystal size and excellent solubility, no additional pretreatment procedure is required before the sucralose crystal product is used, which simplifies the process flow.

The above are merely specific embodiments of the present disclosure, and under the above teaching of the present disclosure, those skilled in the art may make other improvements or variations on the basis of the above examples. Those skilled in the art should understand that the above specific description is merely intended to well explain the objects of the present disclosure, and the protection scope of the present disclosure shall be subject to the protection scope of the claims.

Furthermore, it will be understood by those skilled in the art that although some of the embodiments described herein include certain features included in other embodiments and not others, the combination of features of different embodiments means that they are within the scope of the present application and form different embodiments. For example, in the following claims, any one of the embodiments claimed to be protected may be used in any combination.

What is claimed is:

1. A method for purifying sucralose, sequentially comprising:

- adding sucralose to ultrapure water (UPW) to obtain a mixture, heating the mixture to obtain a dissolved solution, and filtering the dissolved solution to obtain a recrystallization solution;
- extracting the recrystallization solution with an extraction solvent to remove non-polar impurities to obtain an extracted recrystallization solution;
- subjecting the extracted recrystallization solution to concentration by evaporation to obtain a concentrated recrystallization solution with a preset concentration, and leaving the concentrated recrystallization solution to stand at a preset temperature for a preset time to produce a sucralose crystal nucleus in the concentrated recrystallization solution;
- subjecting the concentrated recrystallization solution containing the sucralose crystal nucleus to gradient cooling to obtain a recrystallization solution with a large amount of a sucralose crystal; and
- centrifuging the recrystallization solution with a large amount of a sucralose crystal to obtain a solid, and subjecting the solid to water-washing and drying to obtain the sucralose crystal; wherein
- the preset concentration is in a range of 60 wt % to 80 wt %;
- the preset temperature is in a range of 50° C. to 60° C.; and
- the preset time is in a range of 0.5 h to 3 h; and
- the gradient cooling comprises:
  - cooling the concentrated recrystallization solution containing the sucralose crystal nucleus from a first temperature of 52° C. to 58° C. to a second temperature of 43° C. to 47° C. at a first cooling rate of 1° C./10 min to 1° C./60 min,
  - holding at the second temperature for 0.5 h to 3 h, and cooling to a third temperature of 18° C. to 22° C. at a second cooling rate of 1° C./10 min to 1° C./60 min.

2. The method of claim 1, wherein the sucralose has an original purity of 98.0% to 99.6%, a residue on ignition of 0.70 wt % to 0.10 wt %, and a moisture content of 2.0 wt % to 0.30 wt %.

3. The method of claim 2, wherein the sucralose has the original purity of 99.0% to 99.5%, a residue on ignition of 0.20 wt % to 0.10 wt %, and the moisture content of 0.50 wt % to 0.30 wt %.

4. The method of claim 1, wherein the UPW has a resistivity of greater than 18.0 MΩ-cm; and based on a mass of the sucralose, a ratio of a volume of the UPW to the mass of the sucralose is in a range of 0.5 to 4.0 mL/g.

5. The method of claim 4, wherein the UPW has the resistivity of 18.3 MΩ-cm;

and based on the mass of the sucralose, the ratio of the volume of the UPW to the mass of the sucralose is in a range of 1.0 to 3.0 mL/g.

6. The method of claim 1, wherein the heating is conducted at 25° C. to 50° C., and the heating is conducted for 10 min to 8 h; and the filtering is conducted with a precision pipeline filter of more than 800 mesh.

7. The method of claim 6, wherein the heating is conducted at 35° C. to 45° C., and the heating is conducted for 20 min to 4 h.

8. The method of claim 1, wherein the extraction solvent comprises ethyl acetate or isopropyl acetate; and a volume ratio of the extraction solvent to the recrystallization solution is in a range of 0.5 to 8.0.

9. The method of claim 8, wherein the extraction solvent comprises the ethyl acetate or the isopropyl acetate; and the volume ratio of the extraction solvent to the recrystallization solution is in a range of 1.0 to 4.0.

10. The method of claim 1, wherein the concentration by evaporation is conducted at a temperature of 45° C. to 60° C. for 10 min to 12 h.

11. The method of claim 10, wherein the preset temperature is in a range of 52° C. to 58° C.; and the preset time is in a range of 0.5 h to 2 h.

12. The method of claim 1, wherein the gradient cooling is conducted as follows: cooling the concentrated recrystallization solution containing the sucralose crystal nucleus from the first temperature of 52° C. to 58° C. to the second temperature of 45° C. at the first cooling rate of 1° C./10 min to 1° C./60 min, and holding at the second temperature for 0.5 h to 3 h, and then cooling to the third temperature of 20° C. at the second cooling rate of 1° C./10 min to 1° C./60 min.

* * * * *